United States Patent
Kim

(10) Patent No.: US 12,029,913 B2
(45) Date of Patent: Jul. 9, 2024

(54) SYNTHETIC TREATMENT APPARATUS HAVING REPLACEABLE HEAD

(71) Applicant: INTIN CO., LTD., Daegu-si (KR)

(72) Inventor: Ji Hoon Kim, Seoul (KR)

( * ) Notice: Subject to any disclaimer, the term of this patent is extended or adjusted under 35 U.S.C. 154(b) by 262 days.

(21) Appl. No.: 16/969,560

(22) PCT Filed: Aug. 13, 2019

(86) PCT No.: PCT/KR2019/010279
§ 371 (c)(1),
(2) Date: Aug. 13, 2020

(87) PCT Pub. No.: WO2020/111445
PCT Pub. Date: Jun. 4, 2020

(65) Prior Publication Data
US 2021/0283418 A1    Sep. 16, 2021

(30) Foreign Application Priority Data
Nov. 30, 2018  (KR) .................. 10-2018-0152730

(51) Int. Cl.
*A61N 5/06* (2006.01)
*A61M 1/00* (2006.01)
(Continued)

(52) U.S. Cl.
CPC .......... *A61N 5/0603* (2013.01); *A61M 1/76* (2021.05); *A61M 1/84* (2021.05); *A61M 11/005* (2013.01);
(Continued)

(58) Field of Classification Search
CPC .................. A61N 5/0603; A61N 5/067; A61N 2005/0604; A61N 2005/0605;
(Continued)

(56) References Cited

U.S. PATENT DOCUMENTS 8,728,136 B2   5/2014  Feldman
2008/0140164 A1*  6/2008  Oberreiter ............ A61N 5/0616
606/9

(Continued)

FOREIGN PATENT DOCUMENTS

CH    349032 A    9/1960
CN   1788807 A    6/2006
(Continued)

OTHER PUBLICATIONS

English Machine Translation of KR-101448860-B1 provided by Espacenet (Year: 2014).*

(Continued)

*Primary Examiner* — Joseph D. Boecker
*Assistant Examiner* — Brian T Khong
(74) *Attorney, Agent, or Firm* — ANTONIO HA & U.S. PATENT, LLC

(57) ABSTRACT

The present invention provides a synthetic treatment apparatus which comprises: a connection part in which treatment part modules are replaced and are connected to or separated from each other, the treatment part modules performing inhalation, suction, light emitting, and aerosol functions, respectively, which are required for treatment for a respiratory disease and ear disease; a power part for supplying power to the treatment part modules according to an operation of a power switch; and a control part for controlling the power module and functions of the treatment part modules, wherein a grip part is formed on the outside of a body in which the power part and the control part are embedded. The present invention can treat various ear and respiratory diseases by replacing a head of the apparatus.

4 Claims, 11 Drawing Sheets

(51) Int. Cl.
*A61M 11/00* (2006.01)
*A61M 11/02* (2006.01)
*A61M 15/00* (2006.01)
*A61M 16/00* (2006.01)
*A61N 5/067* (2006.01)

(52) U.S. Cl.
CPC ........ *A61M 11/02* (2013.01); *A61M 15/0085* (2013.01); *A61M 16/0063* (2014.02); *A61M 16/022* (2017.08); *A61M 2205/051* (2013.01); *A61M 2205/3576* (2013.01); *A61M 2205/52* (2013.01); *A61M 2205/583* (2013.01); *A61N 2005/0604* (2013.01); *A61N 2005/0605* (2013.01); *A61N 2005/0607* (2013.01); *A61N 2005/0626* (2013.01); *A61N 2005/0644* (2013.01); *A61N 2005/0651* (2013.01); *A61N 5/067* (2021.08)

(58) Field of Classification Search
CPC .... A61N 2005/0606; A61N 2005/0607; A61N 2005/0644; A61N 2005/0651; A61M 16/022; A61M 16/0063; A61M 15/06; A61M 15/08; A61M 15/085; A61M 15/0085; A61M 15/001; A61M 1/76; A61M 1/84; A61M 11/005; A61M 11/02; A61H 2201/0153; A61H 2201/0157; A61H 2205/022; A24F 40/40; A24F 40/42; A24F 40/50; A24F 40/65; A24F 40/90; A24F 40/95
See application file for complete search history.

(56) References Cited

U.S. PATENT DOCUMENTS

| | | | |
|---|---|---|---|
| 2012/0232618 A1 | 9/2012 | Feldman | |
| 2013/0008435 A1* | 1/2013 | Feng | A61M 16/0051 128/202.16 |
| 2014/0128780 A1* | 5/2014 | Kennedy | A61B 17/12118 604/20 |
| 2015/0100002 A1* | 4/2015 | Choi | A61N 7/00 604/20 |
| 2015/0128971 A1* | 5/2015 | Verleur | H02J 7/0045 131/329 |
| 2017/0056685 A1 | 3/2017 | Harvey et al. | |
| 2017/0333727 A1 | 11/2017 | Kim et al. | |
| 2017/0367471 A1* | 12/2017 | Straka | A46B 15/0044 |
| 2018/0369459 A1 | 12/2018 | Abate et al. | |
| 2019/0067952 A1* | 2/2019 | Kirchoff | A24F 40/90 |

FOREIGN PATENT DOCUMENTS

| | | | | |
|---|---|---|---|---|
| CN | 105534634 A | | 5/2016 | |
| CZ | 349032 A | * | 9/1960 | ............ A61H 37/00 |
| JP | 2002-058737 A | | 2/2002 | |
| JP | 3090698 U | | 12/2002 | |
| KR | 20-0380310 | | 3/2005 | |
| KR | 10-2010-0119202 | | 11/2010 | |
| KR | 10-1135140 | | 4/2012 | |
| KR | 10-1431201 | | 8/2014 | |
| KR | 10-1448860 | | 10/2014 | |
| KR | 101448860 B1 | * | 10/2014 | .......... A61C 1/0046 |
| KR | 10-2016-0024207 | | 3/2016 | |
| KR | 10-2016-0055082 | | 5/2016 | |
| KR | 10-1650845 | | 8/2016 | |
| KR | 101650845 B1 | * | 8/2016 | ............... A61N 5/06 |
| KR | 10-2017-0108530 | | 9/2017 | |
| WO | 2011-067752 | | 6/2011 | |
| WO | WO2017/141278 | | 8/2017 | |

OTHER PUBLICATIONS

English Machine Translation of KR-101650845-B1 provided by Espacenet (Year: 2016).*
English Machine Translation of CH-349032-A provided by Espacenet (Year: 1960).*
English Abstract of 20-0380310.
English Abstract of 10-1650845.
English Abstract of 10-2016-0055082.
English Abstract of 10-1431201.
May 2011, non-officialtranslation (Mini. Dolphin Multi-tunc a Nebilizer. Babybelle. Product Infomat the Same Model Launched in May 200.
English Abstract of 10-1135140.
English Abstract of 10-1448860.
English Abstract of 10-2010-0119202.
English Abstract of 10-2016-0024207.
English Abstract of 10-2017-0108530.
English Specification of CH349032A.
English Specification of CN1788807A.
English Specification of CN105534634A.
English Specification of JP2002-058737A.

* cited by examiner

SYNTHETIC TREATMENT APPARATUS HAVING REPLACEABLE HEAD

TECHNICAL FIELD

The present disclosure relates to a complex treatment apparatus having a replaceable head, and more particularly, to a complex treatment apparatus that may be used for treatment of various types of diseases by replacing a main body corresponding to a treatment part module having a corresponding function.

BACKGROUND ART

Medical apparatuses used to treat respiratory diseases, such as asthma, include nebulizers, metered dose inhalers (MDIs), spacers and dry powder inhalers (DPIs). In addition, there is a suction device used to remove sputum or the like in relation to respiratory diseases.

Among the respiratory disease treatment apparatuses is a luminescence treatment apparatus used to treat inflammation of a nose or ear, not an airway. Semiconductor devices used as light sources in light therapy include light emitting diodes (LEDs) and laser diodes (LDs). There are many similarities between LEDs and LDs as semiconductor devices, but LEDs and LDs are different in that the former uses natural emission of light while latter uses induced emission of light.

In particular, light amplification by stimulated emission of radiation (LASER) refers to amplification of light rays by induced emission of radiation and has characteristics such as monochromaticity, focusability, high density, and the like.

Irradiation of light in a red-near infrared range to human tissues has been proven to be effective in healing wounds, inflammation, and edema of living tissues and reducing peripheral neuralgia by clinical tests. In these clinical tests, a low level laser therapy (LLLT) method is used.

In the related art described above, the nebulizer, the suction device, the inhaler, and the luminescence treatment apparatus are configured as independent devices, and there is a disadvantage in that economic efficiency deteriorates due to overlapping facilities between devices that exhibit similar functions. In addition, the related art involves inconvenience in that a user must visit a doctor even when a treatment is possible at home according to a doctor's treatment.

The complex treatment apparatus according to an embodiment of the present disclosure includes a replaceable head corresponding to a treatment part module, so that the nebulization, inhalation, suction, and luminescence functions necessary for a treatment of respiratory diseases and nasal diseases may be performed in combination. In this sense, the complex treatment apparatus according to an embodiment of the present disclosure is distinguished from the related art described above and disclosed to solve the problems of the related art.

DISCLOSURE

Technical Problem

An aspect of the present disclosure provides a complex treatment apparatus capable of treating various ear and respiratory diseases through head replacement.

Another aspect of the present disclosure provides a complex treatment apparatus capable of automatically recognizing a head and selecting an operation mode according to head replacement based on a treatment method.

Another aspect of the present disclosure provides a complex treatment apparatus capable of recognizing a head to be replaced in a main body, controlling an operation thereof, and displaying an operation state through a liquid crystal display (LCD).

Technical Solution

According to an aspect of the present disclosure, a complex treatment apparatus includes a connection part to or from which treatment part modules respectively performing inhalation, suction, luminescence, and nebulization functions required for treatment of respiratory diseases and ear diseases are replaceably connected or separated; a power supply part configured to supply power to the treatment part modules according to an operation of a power switch; and a controller configured to control functions of the power supply part and the treatment part modules, wherein a grip part is provided outside a main body in which the power supply part and the controller are installed.

Here, the connection part may include a connector electrically connecting a first PCB with the power supply part and the controller installed therein and a second PCB with a display part displaying the functions of the treatment part modules.

Here, the connection part may further include a fastening ring or a fastening hook configured to support the fastened connector not to be released, the fastening ring configured to use rotational coupling through screw thread.

Here, the controller may include: a recognition module configured to recognize an ID assigned to a treatment part module connected through the connector; and a mode selection module configured to select an operation mode suitable for the recognized treatment part module.

Here, the controller may control the display part included in a corresponding treatment part module according to the selected operation mode.

Here, the complex treatment apparatus may include, as a treatment part module, at least one of a luminescence treatment apparatus using a laser or LED light, a nebulizer configured to perform nebulizing using an ultrasonic wave or a motor, and an inhaler and a suction device using a compressor, connected through the connection part.

Here, the controller may further include: a communication module configured to transmit data regarding treatment history using a corresponding treatment part module to a user terminal.

Advantageous Effects

According to the present disclosure, various ear and respiratory diseases may be treated through head replacement.

In addition, a head may be automatically recognized and an operation mode may be selected according to head replacement based on a treatment method.

In addition, by recognizing a head being replaced in the main body, an operation thereof may be controlled and an operation state may be displayed through the LCD.

BEST MODE FOR INVENTION

Figure 1:
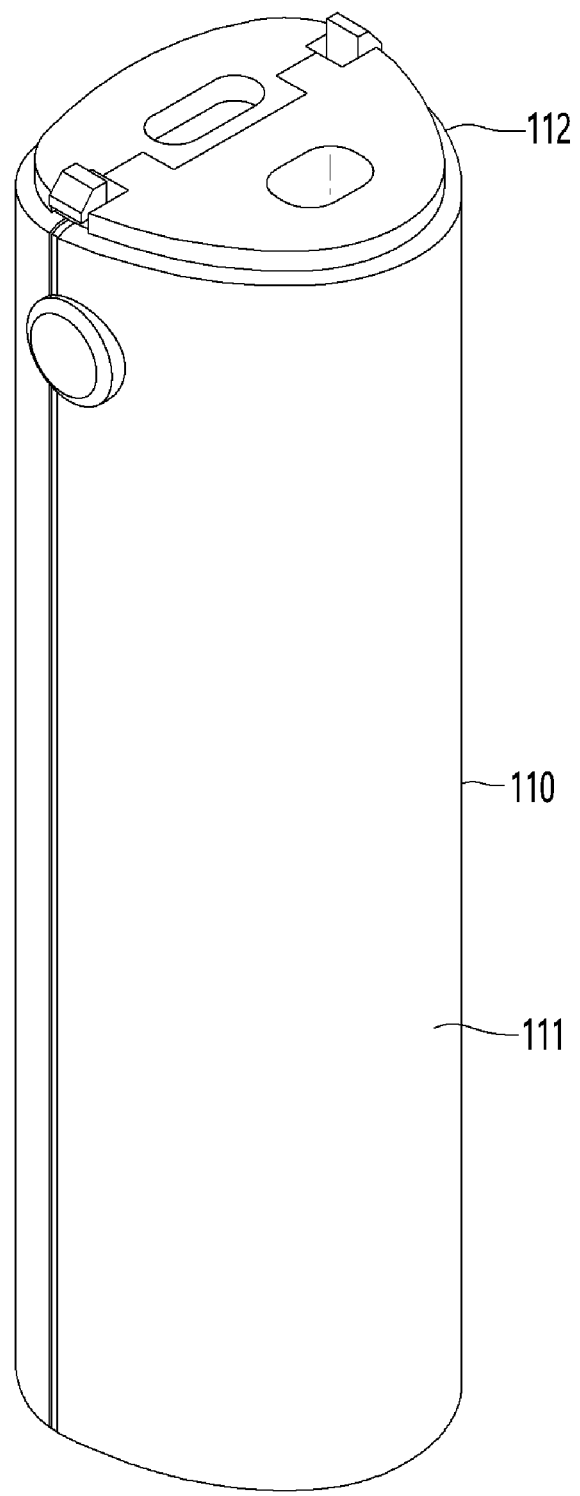
FIG. 1 is an exemplary view of a complex treatment apparatus according to an embodiment of the present disclosure.

Hereinafter, embodiments of a complex treatment apparatus of the present disclosure will be described in detail with reference to the accompanying drawings.

The same constituent elements in the drawings are denoted by the same reference numerals. Specific structural or functional descriptions of the embodiments of the present disclosure are exemplified for the purpose of describing the embodiments of the present disclosure only, and unless defined otherwise, all technical and scientific terms used herein have the same meaning as commonly understood by a person skilled in the art to which the present disclosure pertains. The terms same as ones defined in a commonly-used dictionary should be interpreted as including the meaning in accordance with the meaning in the context of the related art, and should not be interpreted as being ideally or excessively literally unless they are defined clearly in this specification.

FIG. 1 is an exemplary view of a complex treatment apparatus according to an embodiment of the present disclosure.

Referring to FIG. 1, a complex treatment apparatus 100 according to an embodiment of the present disclosure is illustrated.

The complex treatment apparatus 100 has a columnar shape overall and has a cross-section in a curved shape close to a triangular shape, but is not limited thereto. Therefore, the cross-section of the complex treatment apparatus may have various shapes such as a circle, an ellipse, and a polygon, a straight line, and a curved line.

An appearance of the complex treatment apparatus 100 has a shape that is comfortable to be gripped in a hand, and a grip part 111 is provided outside a main body 110. A connection part 112 is realized at one end of the complex treatment apparatus 100, and treatment part modules 210 to 240 may be connected and separated through the connection part 112. Here, the treatment part modules 210 to 240 perform inhalation, suction, luminescence, and nebulization functions required for treating respiratory diseases and diseases, respectively, and correspond to a head or probe for the complex treatment apparatus 100. Hereinafter, the treatment part modules 210 to 240 will be briefly described.

The complex treatment apparatus 100 includes, as a treatment part module, at least one of a luminescence treatment apparatus using a laser or LED light, a nebulizer configured to perform nebulizing using an ultrasonic wave or a motor, an inhaler and a suction device using a compressor, and a beauty appliance, connected through the connection part. Here, examples of the beauty appliance may include a galvanic face massager, an LED skin manager, a vibration massager, and a plasma skin manager.

Figure 2:
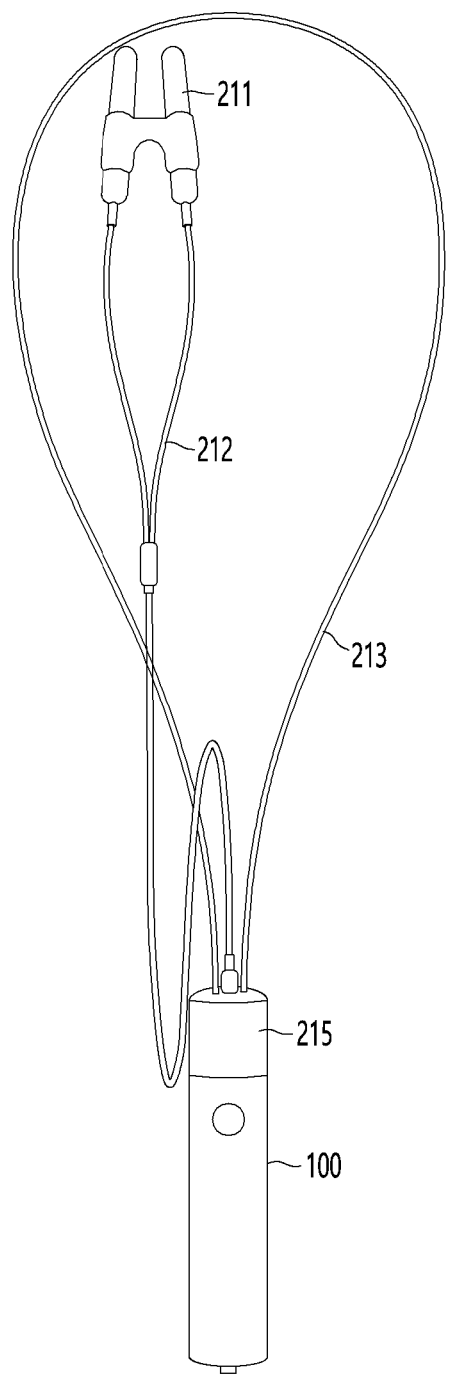
FIG. 2 is an exemplary view of a luminescence treatment apparatus according to an embodiment of the present disclosure.

FIG. 2 is an exemplary view of a luminescence treatment apparatus according to an embodiment of the present disclosure.

Referring to FIG. 2, a combined body in which a luminescence treatment apparatus 210 and a complex treatment apparatus 100 are coupled through the connection part 112 illustrated.

A cable 212 serves to connect a probe 211 and a body 215 connected to the main body 100. Various electrical signals, such as current and control signals, are transmitted through the cable 212. One end of the cable 212 is connected to the probe 211 and the other end thereof is connected to the body 215. At one end, the cable 212 may be integrally connected to the probe 211 or connected to be fastened and separated through a plug and socket configuration. The cable 212 at the other end may be connected to be fastened to and separated from the main body 100 through a plug and socket configuration.

A strip 213 corresponds to a strip for a necklace that is connected to the body 215 or the main body 100. Hereinafter, the interior of the complex treatment apparatus will be described with reference to FIG. 3.

Figure 3:
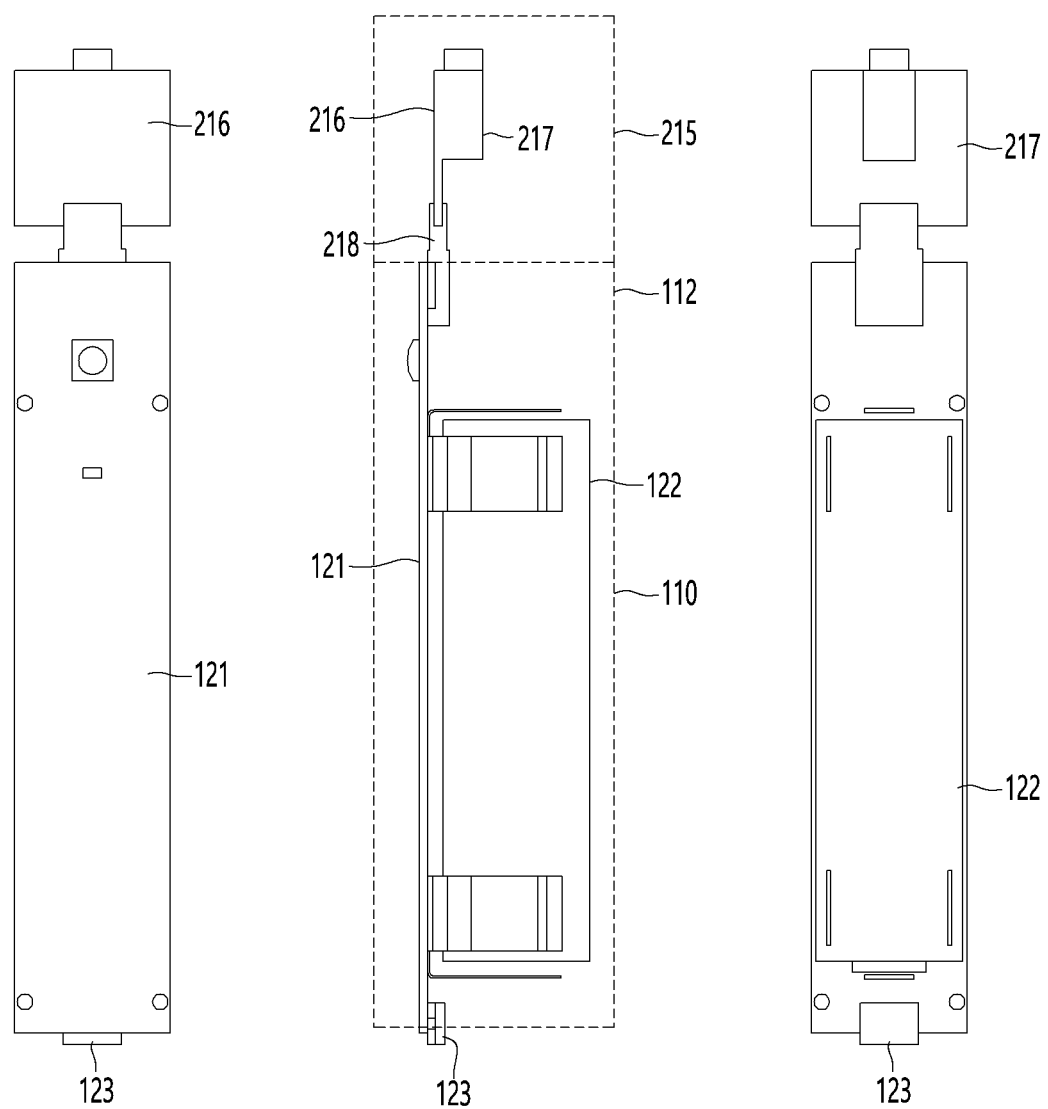
FIG. 3 is an exemplary view showing an interior of a complex treatment apparatus according to an embodiment of the present disclosure.

FIG. 3 is an exemplary view showing an interior of a complex treatment apparatus according to an embodiment of the present disclosure.

Referring to FIG. 3, rear, left, and front sides regarding the main body 110 of the complex treatment apparatus 100 are illustrated. The body 215 of the treatment part module 210 includes a second printed circuit board (PCB) 216, a socket 217, and a connector 218, and the main body 110 includes a first PCB 121, a battery 122, and a connector 123.

The body 215 of the treatment part module 210 includes the second PCB 216 regarding a driver driving a light source part 251, and the main body 110 includes the first PCB 121 regarding a controller 131 and a power supply part 135.

The main body 110 of the complex treatment apparatus 100 and the body 215 of the treatment part module 210 may be connected through the connector 218 of the connection part 112. That is, the connection part 112 includes the connector 218 electrically connecting the first PCB 121 having the power supply part and the controller installed therein and the second PCB 216 having the display part displaying the functions of the treatment part modules installed therein.

The complex treatment apparatus 100 may further include a fastening ring that supports the fastened connector not to be released, the fastening ring may use rotational coupling through screw thread. In addition, the main body 110 and the body 215 fastened through the connector 218 may be firmly fixed using a fastening hook 219. These will be described with reference to FIGS. 10 and 11 hereinafter.

Figure 4:
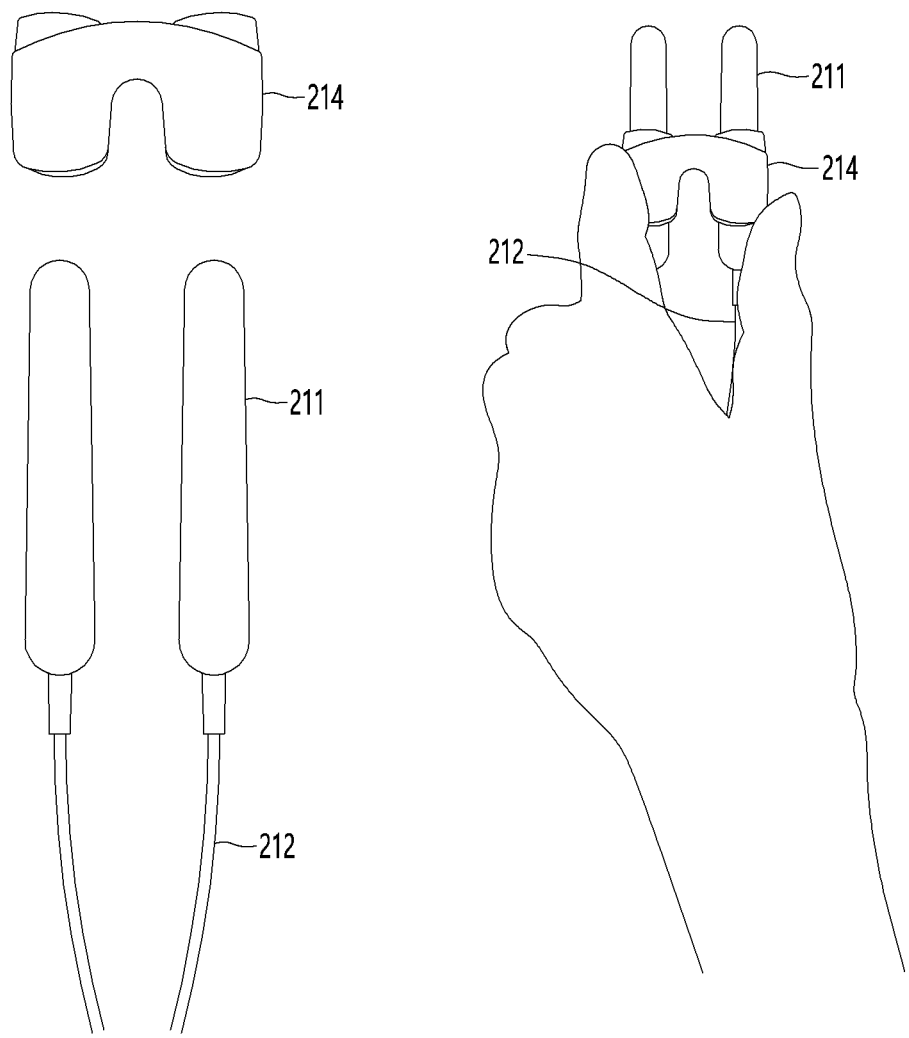
FIG. 4 is an exemplary view of a luminescence treatment apparatus according to an embodiment of the present disclosure.

FIG. 4 is an exemplary view of a luminescence treatment apparatus according to an embodiment of the present disclosure.

The probe 211 is a pair, and each piece is configured separately from each other. Each piece of the probe 211 may be inserted into a holder 214. The holder 214 may be formed of an elastic material, for example, a silicone material. A shape of the holder 214 is not limited to FIG. 4, and the holder 214 may include various shapes in which an interval between the pieces thereof may be uniformly maintained or elastically adjusted.

Figure 5:
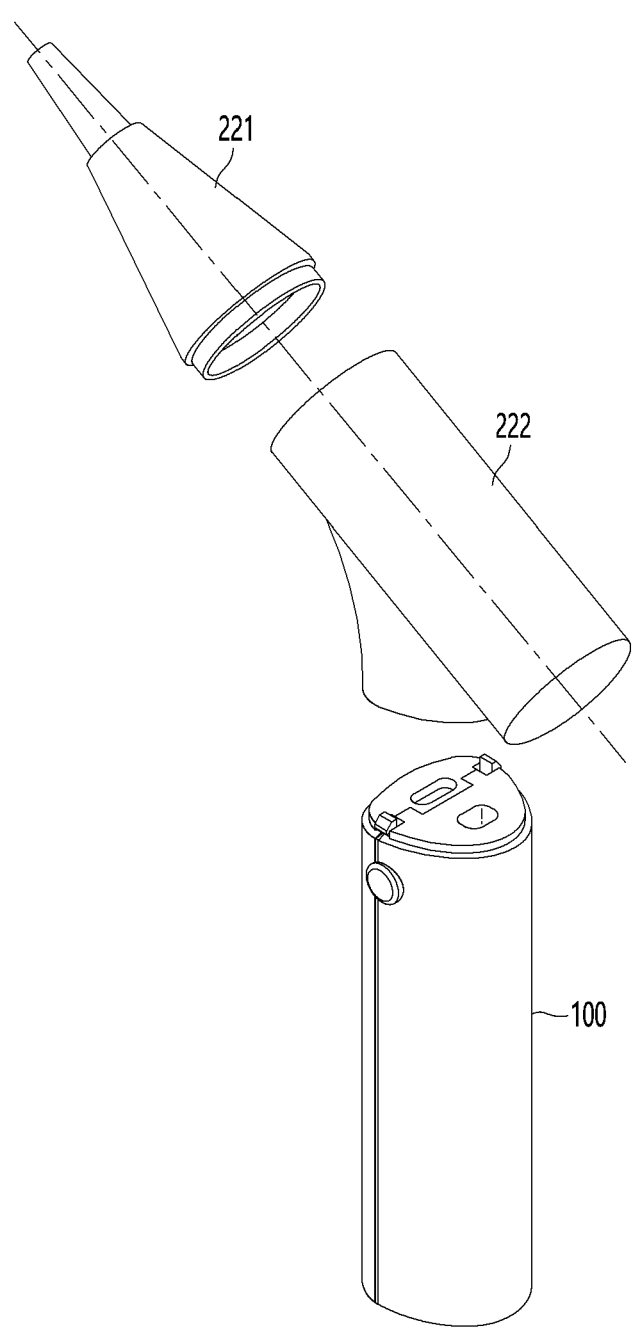
FIG. 5 is an exemplary view of a suction device or an inhaler according to an embodiment of the present disclosure.
Figure 6:
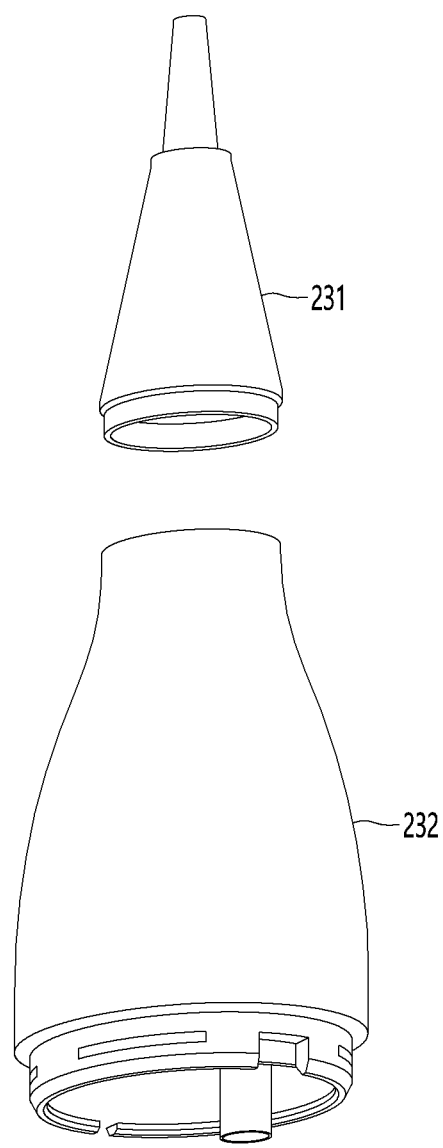
FIG. 6 is an exemplary view of a suction device or an inhaler according to an embodiment of the present disclosure.

FIGS. 5 and 6 are exemplary views of a suction device and an inhaler according to an embodiment of the present disclosure.

Referring to FIGS. 5 and 6, directions in which functions of the suction device and the inhaler are performed are the opposite to each other. Therefore, the suction device and the inhaler may be realized in the same shape.

FIG. 5 is a gun type in which a nozzle is formed in a diagonal shape with respect to the grip part, and FIG. 6 is a pen type in which a nozzle is formed in a linear direction with respect to the grip part. In FIG. 5, a direction of the nozzle formed with the grip part may vary within a range of 90 degrees to 180 degrees.

The suction device, a device that removes foreign substances in the nose or bronchi, for example, sputum or the like, performs inhalation function using compressed air. Therefore, the suction device 220 includes a compressor 224 as an internal component thereof. The compressor may be configured in a body 222. A nozzle part 221 and the body 222 are coupled, and the body 222 is coupled to the main body 100 through the connection part 122. The body 222 of the suction device 220 may include an LCD screen displaying an operation state and various information by a display part. The suction device includes a space for storing foreign substances sucked therein, in the form of a plastic bin.

The inhaler is a device used to intake a liquid drug or a powdered drug. According to the related art, compressed gas is used. In the present disclosure, compressed gas may be used as in the related art or compressed air may be used through the compressor. The inhaler has a space for storing drugs or capsules therein. In FIG. 6, a nozzle part 231 and a body 232 are formed in a linear direction as described above.

Figure 7:
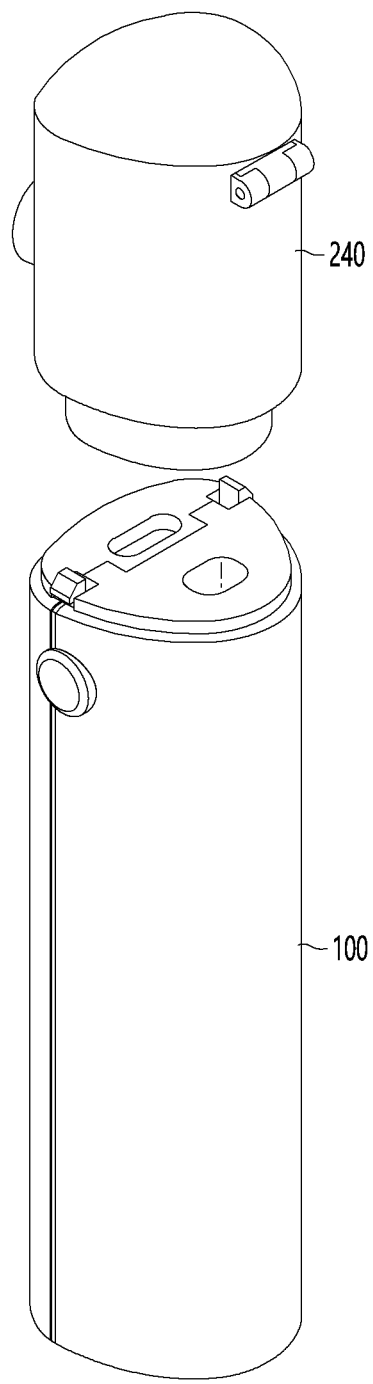
FIG. 7 is an exemplary view of a nebulizer according to an embodiment of the present disclosure.

FIG. 7 is an exemplary view of a nebulizer according to an embodiment of the present disclosure.

Referring to FIG. 7, an intake port is provided on the left of the body 240. The body 240 includes an ultrasonic module 244 or a motor therein. Mist is converted into water vapor by the operation of the ultrasonic module or motor and discharged through the intake port. Hot water vapor may be generated by increasing a temperature in the process of transforming a drug into water vapor.

Figure 8:
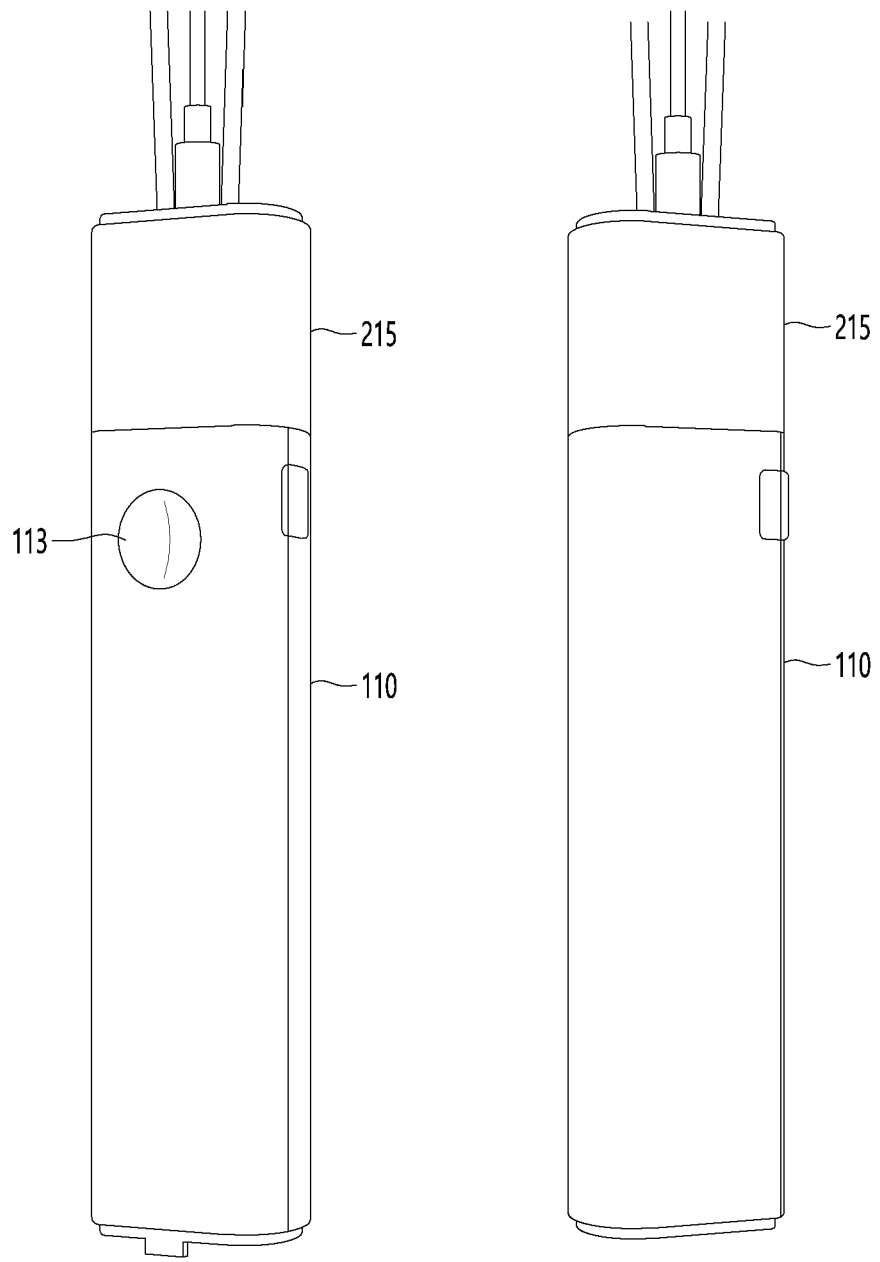
FIG. 8 is an exemplary view showing an exterior of a complex treatment apparatus according to an embodiment of the present disclosure.

FIG. 8 is an exemplary view showing an exterior of a complex treatment apparatus according to an embodiment of the present disclosure.

Referring to FIG. 8, for example, in case of the luminescence treatment apparatus 210 illustrated in FIG. 2, a power switch 113 is provided in the main body 110 of the complex treatment apparatus 100.

Figure 9:
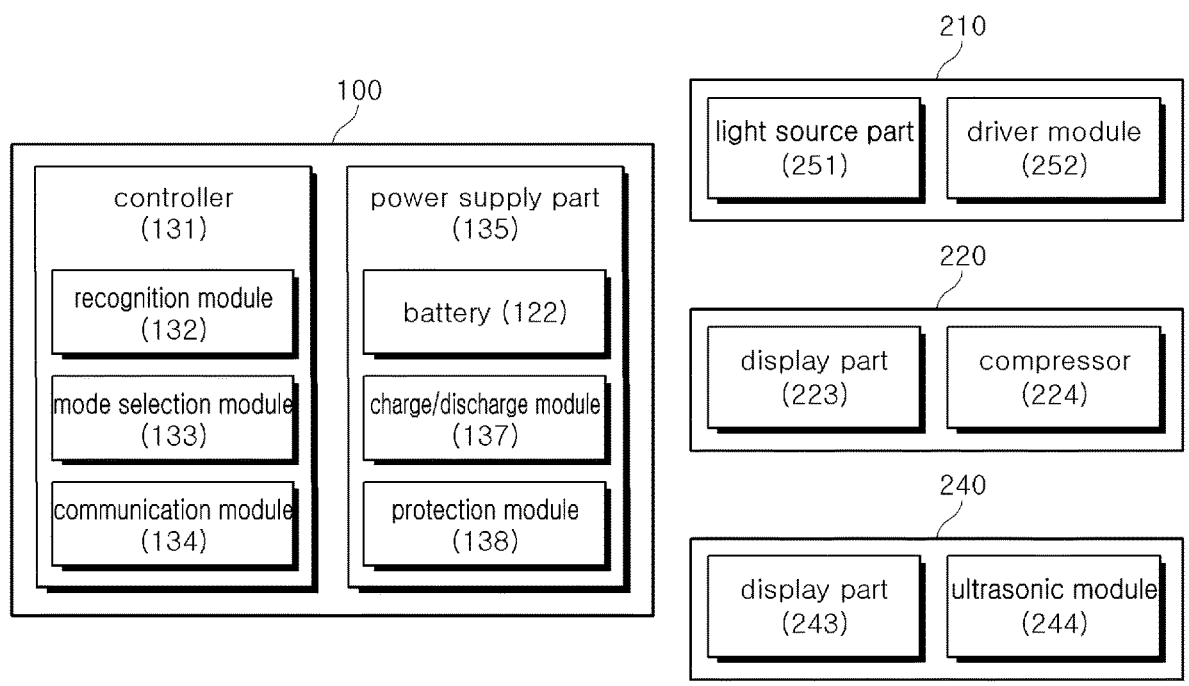
FIG. 9 is a block diagram of a complex treatment apparatus according to an embodiment of the present disclosure.

FIG. 9 is a block diagram of a complex treatment apparatus according to an embodiment of the present disclosure.

Referring to FIG. 9, the main body 110 includes the controller 131 and the power supply part 135 including a battery 122, a charge/discharge module 137, and a protection module 138 therein.

The controller 131 controls the functions of the power supply part 135 and the treatment part modules. The power supply part 135 supplies power to the treatment part modules 210 to 240 according to the operation of the power switch 113.

The controller 131 includes a recognition module 132, a mode selection module 133, and a communication module 134.

The recognition module 132 serves to recognize an ID assigned to a treatment part module connected through the connector 218. The plurality of treatment part modules 210 to 240 each have a unique ID. When the complex treatment apparatus 100 and a treatment part module are connected to each other and power is supplied, the treatment part module transmits unique ID information thereof to the complex treatment apparatus 100, and the complex treatment apparatus 100 identifies the treatment part module through the received unique ID information.

The mode selection module 133 serves to select an operation mode suitable for the recognized treatment part module. When the connected treatment part module is identified, the mode selection module 133 selects a mode to perform a function corresponding to the connected treatment part module. That is, when the suction device 220 having a suction function is connected, the mode selection module 133 selects a suction device mode and is ready to control the suction device 220.

Referring to FIG. 9, a block diagram of the luminescence treatment apparatus 210, the suction device or inhaler 220, and a nebulizer 240 is shown. Among them, the suction device 220 and the nebulizer 240 include display parts 223 and 243, respectively.

The controller 131 controls a display part included in a corresponding treatment part module according to the selected operation mode. Control of power and performance is performed by the controller 131 of the complex treatment apparatus 100. Furthermore, the controller 131 may display an operating state, for example, a pressure value, the amount and temperature of water vapor, through an LCD screen provided outside the body of the treatment part module by controlling a display part included in the treatment part module.

The light source part 251 incudes a kind of a semiconductor device that emits artificial light, for example, a laser diode and an LED. The laser diode and the LED may be selected in various wavelength regions of various ranges depending on the type of LED and laser, for example, a continuous wave method, a pulse method, and treatment portions and symptoms.

A driver module 252 includes a circuit, an oscillator, and a regulator for driving the laser diode or the LED.

In addition, the controller 131 includes a communication module for transmitting data regarding treatment history using the corresponding treatment part module to a user terminal. That is, through short-range communication with the user terminal, the communication module 134 transmits data regarding history of treatment using the corresponding treatment part module according to a type of the treatment part module to the user terminal, and the user terminal may receive the data and store the treatment history data in a storage device.

Various embodiments of the user terminal may include a cellular phone, a smartphone having a wireless communication function, a personal digital assistant (PDA) having a wireless communication function, a wireless modem, a portable computer having a wireless communication function, an image capture device such as a digital camera having a wireless communication function, a gaming device having a wireless communication function, a music storage and playback appliance having a wireless communication function, an Internet home appliance enabling wireless Internet access and browsing, as well as portable units and terminals incorporating combinations of such functions.

Figure 10:
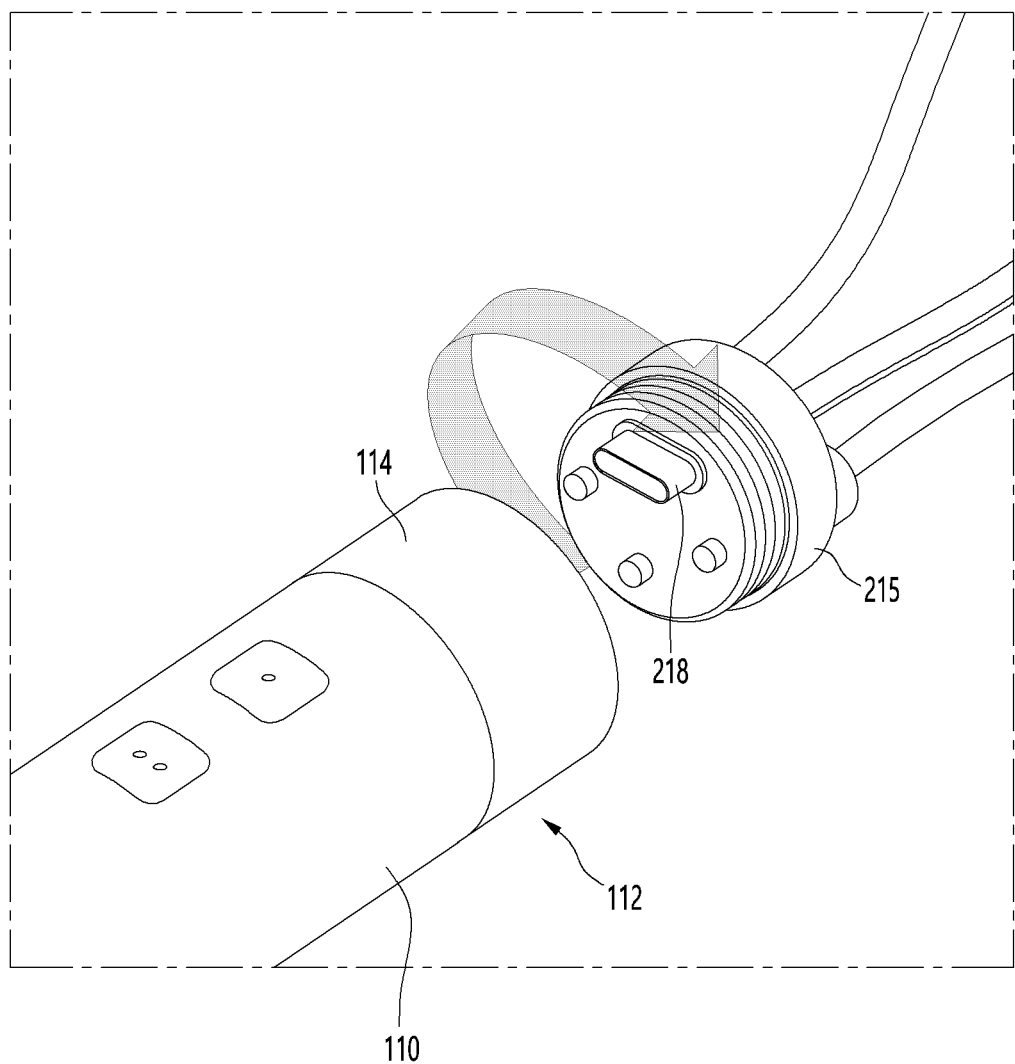
FIG. 10 is an exemplary view illustrating a fastening ring of a complex treatment apparatus according to an embodiment of the present disclosure.

FIG. 10 is an exemplary view illustrating a fastening ring of a complex treatment apparatus according to an embodiment of the present disclosure.

Figure 11:
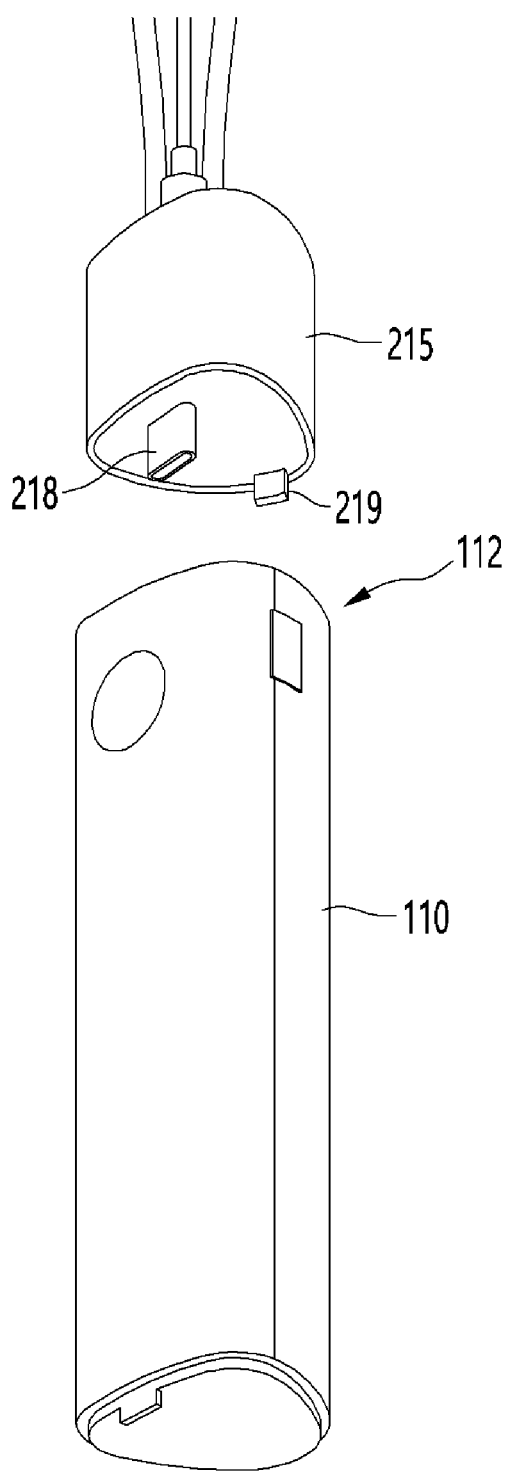
FIG. 11 is an exemplary view illustrating a fastening hook of a complex treatment apparatus according to an embodiment of the present disclosure.

FIG. 11 is an exemplary view illustrating a fastening hook of the complex treatment apparatus according to an embodiment of the present disclosure.

Referring to FIGS. 10 and 11, the connection part 112 further includes a fastening ring 114 or a fastening hook 219 that supports the fastened connector not to be released, the fastening ring 114 configured to use rotational coupling through screw thread.

Referring to FIG. 10, the body 215 and the main body 110 are fastened through the connector 218, and in this fastened state, the main body 110 is firmly fixed to the body 215 by rotating the fastening ring 114 which is not separated through a projection (not shown) in the main body 122.

Referring to FIG. 11, the main body 110 and the body 215 are fastened through the connector 218, and in addition to this, the fastening hook 219 is coupled to firmly fix the main body 110 and the body 215.

As described above, according to an embodiment of the present disclosure, various ear and respiratory diseases may be treated through head replacement.

In addition, the head may be automatically recognized and an operation mode may be selected according to the head replacement based on a treatment method.

In addition, by recognizing the head replaced in the main body, an operation may be controlled and an operation state may be displayed through the LCD.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

The invention claimed is:

1. A complex treatment apparatus comprising:
   treatment part modules in which one of treatment part modules is selected to perform one of inhalation, suction, luminescence, and nebulization functions required for treatment of respiratory diseases and ear diseases;
   a connection part to or from which the treatment part modules are replaceably connected or separated;
   a power supply part configured to supply power to the treatment part modules according to an operation of a power switch; and
   a controller configured to control functions of the power supply part and the treatment part modules,
   wherein a grip part is provided outside a main body in which the power supply part and the controller are installed,
   wherein the connection part comprises a connector electrically connecting a first PCB with the power supply part and the controller installed therein and a second PCB with a display part displaying the functions of the treatment part modules,
   wherein the controller comprises a recognition module configured to recognize an ID assigned to a corresponding treatment part module connected through the connector and a mode selection module configured to select an operation mode suitable for the corresponding treatment part module, and
   wherein the controller controls the display part included in the corresponding treatment part module according to the selected operation mode.

2. The complex treatment apparatus of claim 1, wherein the connection part further comprises a fastening ring or a fastening hook configured to support the fastened connector not to be released, the fastening ring configured to use rotational coupling through screw thread.

3. The complex treatment apparatus of claim 1, wherein the complex treatment apparatus comprises, as the treatment part module, one of a luminescence treatment apparatus using a laser or LED light, a nebulizer configured to perform nebulizing using an ultrasonic wave or a motor, an inhaler and a suction device using a compressor, and a beauty appliance, connected through the connection part.

4. The complex treatment apparatus of claim 1, wherein the controller further comprises a communication module configured to transmit data regarding treatment history using the corresponding treatment part module to a user terminal.

* * * * *